United States Patent [19]

Duff et al.

[11] Patent Number: 5,698,399
[45] Date of Patent: Dec. 16, 1997

[54] DETECTING GENETIC PREDISPOSITION FOR OSTEOPOROSIS

[76] Inventors: Gordon W. Duff, 18 Ashgate Road, Sheffield, S10 3BZ, S Yorks, England; Graham Russell, Ronksley Farm Hollow Meadows, Sheffield, South Yorks S6 6GH, England; Richard Eastell, 289 Ringinglow Road, Sheffield, S11 7PZ, England

[21] Appl. No.: 628,282

[22] Filed: Apr. 5, 1996

[51] Int. Cl.[6] .......................... C12Q 1/68; C12P 19/34
[52] U.S. Cl. ................................... 435/6; 435/91.2
[58] Field of Search ................. 435/6, 91.2; 536/24.3, 536/24.31, 24.33; 514/1, 2

[56] References Cited

U.S. PATENT DOCUMENTS 5,064,851  11/1991  Goddard et al. ...................... 514/406
5,593,833  1/1997   Morrison et al. ...................... 435/6

OTHER PUBLICATIONS

Tarlow et al., J. Inv. Dermatol. 103, 387–390 (1994).
Clay et al., Hum. Genet. 94, 407–410 (1994).
Clay et al., Hum. Genet. 97, 723–726 (1996).
Anderson and Pollitzer, "Ethnic and genetic differences in susceptibility to osteoporotic fractures", *Adv Nutr Res*, 9:129–49 (1994).
Blakemore et al., "Interleukin–1 receptor antagonist gene polymorphism as a severity factor in systemic lupus erythematosus", *Arthrits and Rheumatism*, 37(9):1380–1385 (1994).
Clark et al., "Genomic sequence for human prointerleukin 1 beta: possible evolution from a reverse transcribed prointerleukin 1 alpha gene", *Nucl Acids Res*, 14:7897–7914 (1986).
di Giovine, et al., "Single base polymorphism at –511 in the human interleukin–1β gene (IL–1β)", *Human Molecular Genetics*, 1(6):450 (1992).
Dequeker et al., "Genetic determinants of bone mineral content content at the spine and radius: A twin study", *Bone*, 8:207–209 (1987).
Duff, "Cytokines and anti–cytokines", *Br. J. Rheumatol*, 32 (Suppl 1):15–20 (1993).
Eastell and Riggs, "New approaches to the treatment of osteoporosis", *Clin Obstet Gynecol*, 30(4):860–70 (1987a).
Eastell and Riggs, "Diagnostic evaluation of osteoporosis", *Endocrinol Metab Clin North Am*, 17(3):547–71 (1988).
Eastell and Riggs, "Treatment of osteoporosis", *Obstet Gynecol Clin North AM*, 14(1):77–88 (1987b).
Eastell, "Management of corticosteroid–induced osteoporosis: UK Consensus Group Meeting on Osteoporosis", *J Intern Med*, 23(5):439–47 (1995).

Furutani et al., "Complete nucleotide sequence of the gene for human interleukin 1 alpha", *Nucl Acids Res*, 14:3167–319 (1986).
Garabedian, "Genetic aspects of osteoporosis", *Curr Opin Rheumatol*, 7(3):237–9 (1995).
Kanis et al., "The diagnosis of osteoporosis", *J Bone Miner Res*, 10(6):978–84 (1995).
Kelly et al., "Genetic influences on bone turnover, bone density and fracture", *Eur J Endocrinol*, 133(3):265–71 (1995).
Krall et al., "Vitamin D receptor alleles and rates of bone loss: influences of years since menopause and calcium intake", *J Bone Miner Res*, 10(6):978–84 (1995).
Mansfield et al., "Novel genetic association between ulcerative colitis and the anti–inflammatory cytokine interleukin 1 receptor antagonist", *Gastroenterology*, 106:637–642 (1994).
Matfin, "The role of cytokines in normal and pathological bone states", *Br J Hosp Med*, 49(6):407, 410–5 (1993).
McDowell, T.L. et al., "A genetic association between juvenile rheumatoid arthritis and a novel interleukin–1 alpha polymorphism", *Arthritis Rheum*, 38:221–228 (1995).
McGuire et al., "Variation in the TNF–α promoter region associated with susceptibility to cerebral malaria", *Nature*, 371:508–511 (1994).
Mundy, "Cytokines and growth factors in the regulation of bone remodeling", *J Bone Miner Res*, 8(suppl 2):S505–10 (1993).
Peel and Eastell, "Diagnostic value of estimated volumetric bone mineral density of the lumbar spine in osteoporosis", *J Bone Miner Res*, 9(3):317–20 (1994).
Peel and Eastell, "ABC of rheumatology. OSteoporosis", *BMJ*, 310(6985):989–92 (1995).
Peel and Eastell, "Measurement of bone mass and turnover", *Baillieres Clin Rheumatol*, 7(3):479–98 (1993).
Pocock et al., "Genetic determinants of bone mass in adults. A twin study.", *J Clin Invest*, 80:706–710 (1987).
Poli et al., "Interleukin–6 deficient mice are protected from bone loss caused by estrogen depletion", *EMBO J*, 13(5):1189–96 (1994).
Prockop and Kivirikko, "Collagens: molecular biology, diseases and potentials for therapy", *Annu Rev Biochem*, 64:403–34 (1995).

(List continued on next page.)

*Primary Examiner*—Kenneth R. Horlick
*Attorney, Agent, or Firm*—Jenkens & Gilchrist

[57] ABSTRACT

The present invention relates to methods of predicting the risk of osteoporosis. Specifically, the methods comprise isolating genomic DNA from an individual and determining an allelic pattern for IL-1 receptor antagonist (IL-1ra) in the genomic DNA. The identification of at least one copy of allele 2 indicates increased susceptibility to osteoporosis.

3 Claims, No Drawings

OTHER PUBLICATIONS

Rickard et al., "Proliferative responses to estradiol, 1L–1α and TGFβ by cells expressing alkaline phosphatase in human osteoblast–like cell cultures", *Calcif Tissue Int*, 52(3):227–33 (1993).

Sambrook et al., "Genetics of osteoporosis", *Br J Rheumatol*, 33(11):1007–11 (1994).

Slemenda et al., "Long–term bone loss in men: effects of genetic and environmental factors", *Ann Intern Med*, 117:286–291 (1992).

Smith et al., "Genetic factors in determining bone mass", *J Clin Invest*, 52:2800–2808 (1973).

Basic and Clinical Immunology, 8th Ed. eds Stites, Terr & Parslow, Chapter 9 pp. 105–123.

Tarlow et al., "Polymorphism in human IL–1 receptor antagonist gene intron 2 is caused by variable numbers of an 89–bp tandem repeat", *Human Genetics*, 91:403–404 (1993).

Teegarden et al., "Peak bone mass in young women", *J Bone Miner Res*, 10(5):711–5 (1995).

Tokita et al., "Genetic influences on type I collagen synthesis and degradation: further evidence for genetic regulation of bone turnover", *J Clin Endocrinol Metabol*, 78(6):1461–6 (1994).

Verjans et al., "Polymorphism of the tumor necrosis factor region in relation to disease: An overview", *Rheum Dis Clin North Am*, 18:177–186 (1992).

Wilson et al., "Single based polymorphism in the human Tumor Necrosis Factor alpha (TNFα) gene detectable by Nco1 restriction of PCR product", *Human Molecular Genetics 1*, No. 5:353 (1992).

DETECTING GENETIC PREDISPOSITION FOR OSTEOPOROSIS

BACKGROUND OF THE INVENTION

Technical Field

This invention relates to a method of detecting a predisposition for osteoporosis.

Background Art

In 1993, osteoporosis was identified as "one of the leading diseases of women" by Bernadine Healy, MD, then director of the National Institutes of Health. Complications following osteoporosis fractures are the fourth leading cause of death for women over the age of 65, following heart disease, cancer and stroke. It is the leading cause of disability in the United States and the most common cause of hip fracture. For reviews see in general "A Women Doctor's Guide to Osteoporosis" (Sherrer and Levinson, 1995); "150 Most Asked Questions About Osteoporosis" (Jacobowitz, 1993); and "Osteoporosis: Etiology, Diagnosis, and Management" (Raven Press, 1988), as well as Peel and Eastell (1995) and Eastell and Riggs (1988, 1987a,b).

Twenty-five million Americans suffer from osteoporosis, of which 85% are women. Type 1 osteoporosis, which is postmenopausal osteoporosis stemming from loss of estrogen, affects more than half of all women over 65 and has been detected in as many as 90 percent of women over age 75. Type II or senile osteoporosis which is strictly age related, affects both men and women usually over the age of seventy. Another form of osteoporosis affecting both sexes, is drug-induced, for example, by long-term steroid therapy, known to accelerate bone loss (Eastell, 1995). Patient groups that receive long term steroid therapy include asthmatics (7 million over the age of 18 in the United States) as well as patients with rheumatoid arthritis or other autoimmune diseases. Osteoporosis can also occur in association with an underlying disease such as rheumatoid arthritis (prevalence of 1–2% in the population).

Osteoporosis can be diagnosed, monitored and treated with a variety of methods such as set forth in Patent applications WO9420615, WO9501995 and WO9414844 and see in general "Osteoporosis: Etiology, Diagnosis, and Management" (Raven Press, 1988).

Osteoporosis is responsible for a majority of the 1.5 million bone fractures each year leading to disabilities costing 10 billion dollars in medical, social, and nursing-home costs. Even in the best of hands, up to 40% of patients 65 years of age or older will not survive two years following a hip fracture.

In 1991, one in three American women were 50 years or older. The baby boom generation will begin to enter this age group in 1996. Because the average woman lives some thirty years after menopause, with present trends, osteoporosis threatens to be one of the biggest health threats of modern times.

Lifestyle can be a factor in onset of osteoporosis and in particular can be an important factor in building and maintaining healthy bone mass to prevent osteoporosis. Currently, persons under 65 are more likely than their parents to have had a sedentary lifestyle, bad eating habits, increased alcohol and caffeine intake, and a history of greater medication associated with bone loss. It is also clear that there is a genetic predisposition to the development of osteoporosis (see WO9403633 for a discussion of genetic factors in osteoporosis, particularly pages 2–4 incorporated by reference, as well as Anderson and Pullitzer, 1994; Dequeker et al., 1987; Garabedian, 1995; Kelly et al., 1995; Pocock et al., 1987; Sambrook et al., 1994; Tokita et al., 1994).

It would therefore be useful to be able to identify early those individuals at greatest risk for developing osteoporosis so that the individual can be counseled to make appropriate life style changes or institute other therapeutic interventions. For example, calcium supplements and exercise have been shown to be valuable preventive factors if used during a critical early age window. Hormone replacement therapy (HRT) has also been used successfully to combat osteoporosis occurring after menopause. HRT may be of greatest benefit if used early in the disease process before major bone loss has occurred. Since HRT has potentially serious side-effects, it would be useful for women to known their personal risk level for osteoporosis when making decisions about the use of HRT versus other interventions aimed at reducing the risk of developing osteoporosis.

Some tests have been found that are associated with a risk of osteoporosis as set forth in patent applications EP93113604, WO8808457, WO9311149 and WO9403633. However, none of these applications address genetic variation at the multiple loci controlling cytokine expression and their possible role in osteoporosis. Cytokines have been shown to have a role in bone remodeling. In mice it was shown that one cytokine, IL-6, is a mediator of bone loss secondarily to loss of estrogen. (Poli et al, 1994). Additionally, IL-1 and tumor necrosis factor (TNF) both induce IL6 and have several important actions in bone metabolism Therefore, it was an objective of the present invention to determine if the genes that encode cytokines are implicated in the regulation of bone density and if bone density changes are correlated with osteoporosis. If so, it would be useful to identify the allelic variants of these genes that correlate with disease susceptibility and thereby identify individuals who are at risk for osteoporosis.

None of the above cited applications address cytokine regulation of bone remodeling in osteoporosis and so do not identify all those at risk. Further, those individuals who may be at higher risk by having one or more of these risk factors and a predisposition in addition based on the cytokine aspect of the disease would not be identified.

SUMMARY OF THE INVENTION AND ADVANTAGES

According to the present invention a method for predicting low bone mineral density (BMD) and the rate of bone density loss and thereby a susceptibility to osteoporosis is disclosed. The method includes the steps of isolating DNA from a subject and determining the DNA polymorphism pattern of the gene (IL-1RN) that codes for IL-1 receptor antagonist (IL-1ra). The pattern is then analyzed and individuals expressing a genetic polymorphism pattern at IL-1RN which is over-represented in osteoporosis populations is identified. Individuals so identified can then be treated more aggressively to prevent or retard the occurrence of disease.

The present invention further discloses a kit for the identification of a subject's genetic polymorphism pattern associated with osteoporosis. The kit includes DNA sample collecting means and means for determining a genetic polymorphism pattern, which is then analyzed to determine a subject's susceptibility to osteoporosis. Control samples are also included.

DETAILED DESCRIPTION OF THE PREFERRED EMBODIMENT

According to the present invention an allele of the gene (IL-1RN) for IL-1 receptor antagonist (IL-1ra) was found to be associated with osteoporosis. The invention allows individuals with or without overt disease to be identified who have a genetic predisposition for osteoporosis by detecting the presence of a DNA polymorphism in the gene sequence (IL-1RN) for IL-1ra. Osteoporosis is defined as set forth herein above and further as set forth in "Osteoporosis: Etiology, Diagnosis, and Management" (Raven Press, 1988), as well as Peel and Eastell (1994, 1995) and Eastell and Riggs (1988, 1987a,b). Briefly, osteoporosis is a bone disorder characterized by increased brittleness due to a reduction in bone density.

An allele associated with a reduction in bone density was identified as IL-1RN allele 2 as set forth in the Example herein below. Therefore the method of the present invention identifies carriers of at least one copy of the DNA genetic polymorphism pattern associated with disease risk, IL-1RN allele 2.

The method of the present invention also provides for identifying individuals expressing a multiple genetic polymorphism pattern associated with risk of osteoporosis and who would therefore have an increased risk of osteoporosis. The method provides for isolating genomic DNA from a subject and identifying in the DNA a genetic polymorphism pattern for the IL-1 receptor antagonist (IL-1RN) gene. The DNA is then scanned for a genetic polymorphism pattern for other genes associated with osteoporosis as set forth in patents EP93113604, WO8808457, WO9311149 and WO9403633. Control DNA patterns are run concurrently to allow proper identification of the polymorphism pattern. From this is determined the number of polymorphisms carried by the subject that are associated with osteoporosis risk. This allows a determination of the overall risk factor for osteoporosis.

Polymorphism as used herein refers to variants in the gene sequence. The polymorphisms can be those variations (DNA sequence differences) which are generally found between individuals or different ethnic groups and geographic locations which, while having a different sequence, produce functionally equivalent gene products. Polymorphisms also encompass variations which can be classified as alleles and/or mutations which can produce gene products which may have an altered function, i.e. variants in the sequence which can lead to gene products that are not functionally equivalent. Polymorphisms also encompass variations which can be classified as alleles and/or mutations which either produce no gene product, an inactive gene product or increased gene product. Further, the term is also used interchangeably with allele as appropriate.

Genetic testing is carried out in general as set forth in U.S. Pat. Nos. 4,582,788, 5,110,920 and 5,387,506 for diseases associated with, or caused by, one to two genes, once the genes are identified, to determine the risk of disease for a person carrying a given gene or combination of genes (see for example U.S. Pat. Nos. 4,801,531, 4,666,828 and 5,268, 267) and as set forth in the Example herein below.

Further, according to the present invention, a kit for the identification of a subject's genetic polymorphism pattern associated with the risk of osteoporosis is disclosed. The kit includes DNA sample collecting means and means for determining a genetic polymorphism pattern for IL-1RN. Control DNA samples which show known IL-1RN patterns can be included. Once the individual's pattern is identified, the individual's susceptibility to osteoporosis can be determined.

In the practice of the method of the present invention, and in the kit, the DNA sample is obtained from blood or tissue samples. In a preferred embodiment, the DNA will be obtained from blood cells obtained from a finger prick of the individual with the blood collected on absorbent paper. In a further preferred embodiment, the blood will be collected on an AmpliCard™ (University of Sheffield, Section of Molecular Medicine, Department of Medicine and Pharmacology, Royal Hallamshire Hospital, Sheffield, England S10 2JF). Target sequences in the DNA of the dried blood spots are amplified using the polymerase chain reaction (PCR). Oligonucleotide DNA primers that target the specific polymorphic DNA region within the genes of interest are prepared so that in the PCR reaction amplification of the target sequences is achieved. This embodiment has the advantage of requiring only a small amount of blood and avoids the necessity for venipuncture or a tissue biopsy. Moreover, one dried blood spot can provide enough template DNA for multiple testing, allowing replication of results and testing of multiple loci. However, other means for collecting DNA and determining polymorphism patterns as known in the art can be used.

The amplified DNA sequences from the template DNA are then analyzed to determine the genetic polymorphisms present in the amplified sequences and thereby provide a genetic polymorphism profile of the individual. Control DNA samples of the target DNA polymorphism can be run concurrently.

The clinical expression of many diseases is regulated by cytokine production. Cytokines are peptide signalling molecules that are produced by a wide range of activated cells including activated immune cells such as thymus-derived T lymphocytes (T-cells), B lymphocytes and monocyte/ macrophages. The cytokines include interleukins (IL-1 through IL-17), colony stimulating factors (CSFs) for granulocytes and/or macrophages (CSF-G, CSF-M, CSF-GM), tumor necrosis factors (TNFs $\alpha$ & $\beta$), and interferons (IFN $\alpha$, $\beta$ & $\gamma$). The basic activity of IL-1 includes the combined activities of IL-1$\alpha$, IL-1$\beta$ and IL-1 receptor antagonist (IL-1ra). (For a review, see Duff, 1993; and *Basic and Clinical Immunology*, 8th Ed., 1994, Stites, Terr & Parslow, editors, Chapter 9, pgs. 105–123.). Association of a single cytokine polymorphism and disease states have been found as, for example, in Systemic Lupus Erythematosus (Blakemore et al., 1994), Ulcerative Colitis (Mansfield et al., 1994), juvenile rheumatoid arthritis (McDowell et al., 1995) and cerebral malaria (McGuire et al., 1994).

Cytokines have been shown to have a role in bone remodeling. In mice it was shown that IL-6 is a mediator of bone loss due to loss of estrogen (Poli, 1994). Additionally, IL-1 and tumor necrosis factor (TNF) are involved in the regulation of bone remodeling (Mundy, 1993; Rickard et al., 1993; Matfin, 1993).

A specific polymorphism in DNA sequences coding for IL-1ra was found to be associated with osteoporosis: IL-1RN allele 2. Alleles of this polymorphism site for the gene (IL-1RN) encoding IL-1ra are as follows [Tarlow et al., "Polymorphism in human IL-1 receptor antagonist gene intron 2 is caused by variable numbers of an 86-bp tandem repeat" *Human Genetics* 91:403–404 (1993).

Allele 1 contains four repeats and is 412 bp;
Allele 2 contains two repeats and is 240 bp;
Allele 3 contains three repeats and is 326 bp;
Allele 4 contains five repeats and is 498 bp; and
Allele 5 contains six repeats and is 584 bp.

The individual's polymorphism profile, i.e., allelic type, is then analyzed as set forth in the present invention. Population studies have determined the expected profiles of healthy people and individuals with osteoporosis as determined by the present invention. The individual's polymorphism profile is then matched to the expected profiles and the match determines the predisposition towards osteoporosis.

An odds ratio (approximate relative risk) is derived to test the association between allelic polymorphism pattern (genotype) at the IL-1RN locus and development of disease. This provides predictive information that will be used in the clinical management of osteoporosis. A further odds ratio can be derived for genotypes in addition to IL-1RN associated with osteoporosis.

Further, the present invention provides a method for treating individuals who are susceptible to osteoporosis. The individuals are identified as discussed herein above by isolating genomic DNA from a subject, identifying in the DNA a genetic polymorphism pattern for IL-1 receptor antagonist (IL-1ra) gene IL-1RN, and from this identifying in a subject the presence of at least one copy of IL-1RN allele 2 gene thereby indicating susceptibility to osteoporosis. It is then contemplated that these individuals will be administered an antagonist of IL-1 (II-1α, IL-1β or both).

The term antagonist is used in its broadest sense. An antagonist therapy can be any drug or compound which will block the activity of IL-1. For example, the antagonist can bind to IL-1, inhibit or reduce production of IL-1 or inhibit the effects of IL-1 on cells. Additionally, therapies which modify cellular receptors for so that they are not receptive to IL-1 are also encompassed by the term.

Suitable agents for this use would include antibodies to IL-1 or an IL-1 receptor, soluble IL-1 binding proteins, the IL-1 receptor antagonist, anti-inflammatory cytokines (e.g. IL-6, IL-10, TGFβ), and small molecular weight drugs that suppress the synthesis, release or biological actions of IL-1, TNF, IL-6 and other cytokines involved in stimulating bone resorption or inhibiting bone formation. The antagonists are administered and dosed in accordance with good medical practice, taking into account the clinical condition of the individual, the site and method of administration, scheduling of administration, and other factors known to medical practitioners. The "effective amount" for purposes herein is thus determined by such considerations as are known in the art. The amount must be effective to achieve improvement including but not limited to maintenance of bone density mass and other indicators as are selected as appropriate measures by those skilled in the art. Other indicators can include maintained or increased bone mineral content, increased biochemical markers of bone formation and decreased biochemical markers of bone resorption.

In the method of the present invention, the antagonist can be administered in various ways. It should be noted that the antagonist can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques depending on the route required by the antagonist being used as is known to those skilled in the art. Implants of the compounds are also useful. Known techniques which deliver the antagonist orally, subcutaneously or parenterally including intravenous, intraarterial, intramuscular, intraperitoneally, and intranasal administration as well as intrathecal and infusion techniques and implants and retain the biological activity of the selected antagonist are preferred.

The above discussion provides a factual basis for the present invention and for a kit for the identification of a subject's genetic polymorphism pattern associated with osteoporosis. The identification of those at risk for disease allows preventive measures to be initiated prior to disease onset. Further, those individuals who have two or more risk factors, the susceptible genotype and life-style predispositions or other known genetic predispositions, can be particularly monitored and aggressively treated since their risk of disease is unusually high. The methods used with and the utility of the present invention can be shown by the following example.

EXAMPLE

General Methods

Reactions and manipulations involving nucleic acid techniques, unless stated otherwise, were performed as generally described in Sambrook et al., 1989, *Molecular Cloning: A Laboratory Manual*, Cold Spring Harbor Laboratory Press; polymerase chain reaction (PCR) was carried out generally as described in PCR Protocols: *A Guide To Methods And Applications*, Academic Press, San Diego, Calif. (1990) and methodology as generally described in U.S. Pat. Nos. 4,666,828; 4,683,202; 4,801,531; 5,192,659 and 5,272,057 and McDowell et al., 1995, these cited references incorporated herein by reference.

Subject Selection

Post-menopausal women who had suffered at least one osteoporosis-related fracture were selected in order to evaluate women likely to have significant risk factors (environment, genetic or both). Bone mineral density measurements were made by dual energy x-ray absorptiometry (DEXA) at the first clinic visit or study visit and were used for analysis (Peel and Eastell, 1994). Bone mineral density (BMD) refers to the mineral content contained within a certain amount of bone. For example, if 1 gram of mineral per $cm^2$ of bone is found this gives a BMD of 1.0 $g/cm^2$. BMD is a measure of the strength of bones and their resistance to fracture from osteoporosis. Women who had taken hormone replacement therapy (HRT) for more than three months or who had taken oral corticosteroids were excluded.

Controls were normal post-menopausal women recruited from an epidemiology study. The controls had not received HRT and had no known risk factors for osteoporosis.

Data Analysis $\chi^2$ analysis and "Z" score analysis were used. Analyses were performed with the SAS statistical package. The "Z" score describes the magnitude of deviation from an age corrected mean of bone mineral density at a given anatomical site.

DNA preparation

DNA was extracted from whole blood using a modification of the salt-out method (Nucleon II™, Scotlab, UK).

Genotyping

Genetic polymorphisms associated with the IL-1RN gene were identified as previously described by Tarlow et al. (1993). Following PCR the different alleles were identified on a 2% agarose gel stained with ethidium bromide and visualized under UV light. Negative controls without DNA were performed in each experiment.

PCR Amplification and Product Sizing for Alleles of IL-1RN

PCR Amplification was undertaken as previously described by Tarlow et al. (1993). Enzymes used in PCR were from GIBCO BRL, thermocyclers were either Perkin-Elmer or Biometra.

Intron 2 of the IL-1RN gene contains a variable number tandem repeat (VNTR) region that gives rise to five (5) alleles which were identified as follows:

SCREENING: PCR amplification of genomic templates followed by assessment of the size of the product after separation on agarose gels.

PRIMERS: The following primers were produced in an ABI DNA synthesizer based on the genomic sequences:

5' CTCAGCAACACTCCTAT 3' (SEQ ID No: 1)

5' TCCTGGTCTGCAGGTAA 3' (SEQ ID No: 2)

PCR CONDITIONS:
with 1.75 mM (final concentration) $MgCl_2$ and cycling protocol of
1 cycle at 96° C. for 1 minute;
30 cycles of [94° C. (1 minute), 60° C. (1 minute), 70° C. (1 minute)]; and
1 cycle at 70° C. for 2 minutes.

SIZING

Electrophoresis on 2% agarose gel at 90 V for 45 minutes.

PREDICTED RESULTS FROM SIZING:

Allele 1 contains four repeats and is 412 bp;
Allele 2 contains two repeats and is 240 bp;
Allele 3 contains three repeats and is 326 bp;
Allele 4 contains five repeats and is 498 bp; and
Allele 5 contains six repeats and is 584 bp.

Although there are five known alleles at the IL-1RN locus, alleles 3, 4 and 5 are rare.

RESULTS

Applicants investigated the relationship between carriage of alleles of the IL-1RN gene and bone mineral density (by DEXA scan) in 54 healthy postmenopausal women (mean age 62.3 years, range 52.5–77.8 years) with no history of fractures and in 41 untreated postmenopausal women with vertebral and/or distal forearm fractures (mean age 72.0 years, range 52.7–85.4 years).

The polymorphic region of the IL-1RN gene VNTR was amplified by PCR and the PCR products analyzed by electrophoresis on 2% agarose gels. There was no significant difference in carriage rate of allele 2 between the control group and the fracture group ($\chi^2=1.33$, p=0.25).

Bone mineral density (BMD) was measured by dual emission x-ray absorptiometry (DEXA) (Eastell and Riggs, 1988) at lumbar spine (L2–L4) (LSBMD) and femoral neck (FNBMD). "Z"-scores for BMD were calculated from BMD data from a population group of 310 women aged 50 to 85 years. "Z" scores for LSBMD and FNBMD were compared for women who carried allele 2 and those who did not carry allele 2, as shown herein below. IL-12+ refers to women who are either homozygous for allele 2 (2;2) or heterozygous (1;2), whereas IL-1RN2− refers to women who are homozygous for allele 1 (1;1). This system is treated as a two-allele system for purposes of analysis since alleles 3, 4 and 5 are rare.

| | IL-1RN2+ | IL-1RN2− | p |
|---|---|---|---|
| Healthy Control Group (n = 54) | | | |
| LSBMD "Z" score | +0.04 | +0.25 | 0.2 |
| FNBMD "Z" score | +0.09 | +0.13 | 0.9 |
| Subjects: Vertebral/distal forearm fracture group (n = 41) | | | |
| LSBMD "Z" score | −1.06 | −0.29 | 0.03* |
| FNBMD "Z" score | −0.70 | −0.09 | 0.03* |

The "Z" score deviation from an age corrected norm (mean) of bone density at a given anatomical site shows that normal controls have an average positive "Z" scores (although IL-1RN2+ had lower scores even in normals). The fracture group had negative "Z" scores—that is lower bone densities for their age against the population norm. Importantly, IL-1RN2+ subjects had a lower mean bone density at two sites (more negative "Z" scores) than the women with fractures who were IL1RN2−. The difference between IL-1RN(+) and IL-1RN(−) subjects at the two bone sites measured were statistically significant.

The above data shows that in women with osteoporotic fractures, carriage of allele 2 of the IL-1RN gene is associated with lower BMD. This shows that carriage of allele 2 of the IL-1RN gene is a clinically-useful marker of disease severity, and that in subjects likely to have osteoporosis the gene marker differentiates those with significantly lower bone density with the concomitant propensity to osteoporotic fractures—the most important clinical outcome of osteoporosis.

The present invention therefore provides a method of identifying subjects at risk for severe osteoporosis and low bone density to allow early treatment.

Throughout this application various publications and patents are referenced. Full citations for the referenced publications and patents not included herein above are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Anderson and Pollitzer, "Ethnic and genetic differences in susceptibility to osteoporotic fractures", *Adv Nutr Res*, 9:129–49 (1994).

Blakemore et al., "Interleukin-1 receptor antagonist gene polymorphism as a severity factor in systemic lupus erythematosus" *Arthritis and Rheumatism* 37(9):1380–1385 (1994).

Clark et al., "Genomic sequence for human prointerleukin 1 beta: possible evolution from a reverse transcribed prointerleukin 1 alpha gene" *Nucl Acids Res* 14:7897–7914 (1986) [published erratum appears in *Nucleic Acids Res* 15(2):868 (1987)].

de Giovine et al., "Single base polymorphism at -511 in the human interleukin-1β gene (IL1β)" Human *Molecular Genetics* 1, No. 6:450 (1992).

Dequeker et al., "Genetic determinants of bone mineral content at the spine and radius: A twin study" *Bone*, 8:207–209 (1987).

Duff, "Cytokines and anti-cytokines" *Br. J. Rheumatol* 32 (Suppl 1):15–20 (1993).

Eastell and Riggs, "Diagnostic evaluation of osteoporosis" *Endocrinol Metab Clin North Am* 17(3):547–71 (1988).

Eastell and Riggs, "New approaches to the treatment of osteoporosis" *Clin Obstet Gynecol* 30(4):860–70 (1987a)

Eastell and Riggs, "Treatment of osteoporosis" *Obstet Gynecol Clin North Am* 14(1):77–88 (1987b).

Eastell, "Management of corticosteroid-induced osteoporosis: UK Consensus Group Meeting on Osteoporosis" *J Intern Med* 237(5):439–47 (1995).

Furutani et al., "Complete nucleotide sequence of the gene for human interleukin 1 alpha" *Nucl Acids Res* 14:3167–3179 (1986).

Garabedian, "Genetic aspects of osteoporosis" *Curr Opin Rheumatol,* 7(3):237–9 (1995).

Kanis et al., "The diagnosis of osteoporosis" *J Bone Miner Res,* 9(8):1137–41 (1994).

Kelly et al., "Genetic influences on bone turnover, bone density and fracture" *Eur J Endocrinol,* 133(3):265–71 (1995).

Krall et al., "Vitamin D receptor alleles and rates of bone loss: influences of years since menopause and calcium intake" *J Bone Miner Res,* 10(6):978–84 (1995).

Mansfield et al., "Novel genetic association between ulcerative colitis and the anti-inflammatory cytokine interleukin 1 receptor antagonist" *Gastroenterology* 106:637–642 (1994).

Matfin, "The role of cytokines in normal and pathological bone states" *Br J Hosp Med,* 49(6):407, 410–5 (1993).

McDowell et al., "A genetic association between juvenile rheumatoid arthritis and a novel interleukin-1 alpha polymorphism" *Arthritis & Rheumatism* (in press 1995).

McGuire et al., "Variation in the TNF-α promoter region associated with susceptibility to cerebral malaria" *Nature* 371:508–511 (1994).

Mundy, "Cytokines and growth factors in the regulation of bone remodeling" *J Bone Miner Res,* 8 (suppl 2):S505–10 (1993).

Peel and Eastell, "Diagnostic value of estimated volumetric bone mineral density of the lumbar spine in osteoporosis" *J Bone Miner Res* 9(3):317–20 (1994).

Peel and Eastell, "ABC of rheumatology. Osteoporosis" *BMJ* 310(6985):989–92 (1995).

Peel and Eastell "Measurement of bone mass and turnover" *Baillieres Clin Rheumatol* 7 (3) :479–98 (1993).

Pocock et al., "Genetic determinants of bone mass in adults. A twin study." *J Clin Invest,* 80:706–710 (1987).

Poli et al., "Interleukin-6 deficient mice are protected from bone loss caused by estrogen depletion" *EMBO J,* 13(5):1189–96 (1994).

Prockop and Kivirikko, "Collagens: molecular biology, diseases and potentials for therapy", *Annu Rev Biochem,* 64:403–34 (1995).

Rickard et al., "Proliferative responses to estradiol, IL-1α and TGFβ by cells expressing alkaline phosphatase in human osteoblast-like cell cultures" *Calcif Tissue Int,* 52(3):227–33 (1993).

Sambrook et al., "Genetics of osteoporosis", *Br J Rheumatol,* 33(11):1007–11 (1994).

Slemenda et al., "Long-term bone loss in men: effects of genetic and environmental factors" *Ann Intern Med,* 117:286–291 (1992).

Smith et al., "Genetic factors in determining bone mass" *J Clin Invest,* 52:2800–2808 (1973).

Basic and Clinical Immunology, 8th Ed. eds Stites, Terr & Parslow, Chapter 9, pgs 105–123.

Tarlow et al., "Polymorphism in human IL-1 receptor antagonist gene intron 2 is caused by variable numbers of an 86-bp tandem repeat" *Human Genetics* 91:403–404 (1993).

Teegarden et al., "Peak bone mass in young women" *J. Bone Miner Res,* 10(5):711–5 (1995).

Tokita et al., "Genetic influences on type I collagen synthesis and degradation: further evidence for genetic regulation of bone turnover" *J Clin Endocrinol Metabol,* 78(6):1461–6 (1994).

Verjans et al., "Polymorphism of the tumor necrosis factor region in relation to disease: An overview" *Rheum Dis Clin North Am* 18:177–186 (1992).

Wilson et al., "Single base polymorphism in the human Tumor Necrosis Factor alpha (TNFα) gene detectable by NcoI restriction of PCR product" *Human Molecular Genetics* 1, No. 5:353 (1992).

We claim:

1. A method for predicting risk of osteoporosis in a subject comprising the steps of:
   (a) isolating genomic DNA from a subject; and
   (b) determining an allelic pattern for IL-1 receptor antagonist (IL-1ra) gene IL-1RN in the genomic DNA;
   wherein an allelic pattern consisting of at least one copy of IL-1RN allele 2 indicates increased susceptibility to osteoporosis.

2. The method according to claim 1 wherein said step of determining an allelic pattern comprises amplification with a polymerase chain reaction (PCR) wherein the PCR primer is selected from the group consisting of:
   5' CTCAGCAACACTCCTAT 3' (SEQ ID No: 1); and
   5' TCCTGGTCTGCAGGTAA 3' (SEQ ID No: 2).

3. A method of predicting a patient's susceptibility to osteoporosis comprising the steps of:
   (a) isolating genomic DNA from a patient;
   (b) determining a genetic polymorphism pattern for the IL-1RN gene in the genomic DNA;
   (c) comparing the genetic polymorphism pattern to at least one control sample, wherein the control sample comprises IL-1RN allele 2; and
   (d) identifying at least one copy of IL-1RN allele 2 in said genetic polymorphism pattern;
   wherein said identifying indicates susceptibility to osteoporosis.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:1:

CTCAGCAACA CTCCTAT 17

( 2 ) INFORMATION FOR SEQ ID NO:2:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:2:

TCCTGGTCTG CAGGTAA 17